US008002787B2

(12) United States Patent
Ferreira Da Luz

(10) Patent No.: US 8,002,787 B2
(45) Date of Patent: Aug. 23, 2011

(54) SURGICAL DEVICE AND METHOD FOR CUTANEOUS DETACHMENT OF SKIN

(76) Inventor: Dilson Ferreira Da Luz, Jaboatao dos Guararapes-PE (BR)

(*) Notice: Subject to any disclaimer, the term of this patent is extended or adjusted under 35 U.S.C. 154(b) by 1066 days.

(21) Appl. No.: 10/553,187

(22) PCT Filed: Apr. 13, 2004

(86) PCT No.: PCT/BR2004/000054
§ 371 (c)(1),
(2), (4) Date: Oct. 13, 2005

(87) PCT Pub. No.: WO2004/089228
PCT Pub. Date: Oct. 21, 2004

(65) Prior Publication Data
US 2006/0235456 A1 Oct. 19, 2006

(30) Foreign Application Priority Data
Apr. 14, 2003 (BR) .................................. 0301879

(51) Int. Cl.
*A61B 17/00* (2006.01)
(52) U.S. Cl. ...................................................... 606/190
(58) Field of Classification Search .................. 606/190, 606/204.35, 157, 158, 201; 128/898; 600/235; 604/164.1, 164.11
See application file for complete search history.

(56) References Cited

U.S. PATENT DOCUMENTS

| 5,746,762 | A | * | 5/1998 | Bass ............................. 606/192 |
| 6,974,450 | B2 | * | 12/2005 | Weber et al. ...................... 606/2 |
| 2001/0025190 | A1 | * | 9/2001 | Weber et al. .................... 607/89 |
| 2001/0034535 | A1 | * | 10/2001 | Schultz ........................ 606/190 |
| 2003/0014041 | A1 | * | 1/2003 | Weber et al. ...................... 606/2 |
| 2003/0018350 | A1 | * | 1/2003 | Zucherman et al. .......... 606/190 |
| 2003/0216693 | A1 | * | 11/2003 | Mickley .................. 604/164.01 |
| 2004/0049251 | A1 | * | 3/2004 | Knowlton ..................... 607/101 |

OTHER PUBLICATIONS

John A. McCurdy M.D., A Complete Guid to Cosmetic Facial Surgery, 1981, Fredrick Fell pub, pp. 46-51.*
Luiz S. Toledo M.D., Video-Endoscopic Facelift (Aesthetic Plastic Surgery), 1994, springer, vol. 18, pp. 149-152.*
Lazar J. Greenfield et al. and Thomas Ray Stevenson, Surgery: scientific principles and practice, 1997, Lippincott-Raven, second edition, pp. 2269-2271.*
John A. McCurdy M.D., A Complete Guid to Cosmetic Facial Surgery, 1981, Fredrick Fell pub, pp. 116-120.*

* cited by examiner

*Primary Examiner* — Anhtuan T Nguyen
*Assistant Examiner* — David Eastwood
(74) *Attorney, Agent, or Firm* — The Nath Law Group; Jerald L. Meyer; Robert T. Burns

(57) ABSTRACT

The present invention refers to a device and a method for subcutaneous detachment of the face, the leg, the thigh, the breast, the abdomen and the forehead, facilitating the full detachment of the skin from the underlying (adipose) tissue with substantial reduction in bleeding, better skin cutting quality, lesser amount of post-op edema, decreased surgery time, minimization of ecchymoses, prophylaxis of facial nerve injuries, and above all, minimized formation of post-op hematomas.

20 Claims, 4 Drawing Sheets

SURGICAL DEVICE AND METHOD FOR CUTANEOUS DETACHMENT OF SKIN

FIELD OF THE INVENTION

The present invention is related to a device and method for subcutaneous detachment of face, leg, thigh, breast, abdomen and forehead, facilitating the complete detachment of the skin from the underlying tissue (adipose tissue) with significant bleeding reduction, improved quality of cutaneous flaps, improved post-op edema, reduced surgical procedure time, minimization of ecchymoses, prophylaxis of facial nerve injuries, and most of all, minimized formation of post-op hematoma.

BACKGROUND OF THE INVENTION

The techniques existing to date for performance of cutaneous detachment for plastic surgery of the face use mostly scissors and/or scalpel, and in some cases, cannulas (material used for liposuction—thin cannula) in order to initially facilitate the displacement whereupon the procedure is continued using the scissors.

In the case of the scalpel and/or scissors there occurs a great amount of bleeding, and there is needed exhaustive cauterization of the detached area. In the case of the cannula there also occurs a significant amount of bleeding, requiring meticulous cauterization along the entire detached area, in addition to the risk imposed by the cannula, which due to being hollow, withdraws fat from the subcutaneous tissue of the face, and might cause the creation of depressed regions.

These existing processes for detachment of the facial skin during facelift surgery always entail the following risks: 1) hemorrhages during the surgical procedure, 2) formation of hematoma upon cutaneous closure, with the patient still in the surgery room, forcing the surgeon to reopen and cure the bleeding vessels, 3) formation of hematoma with the patient already in bed after surgery, forcing the entire team to return to the hospital, in order to perform a new surgical procedure on the patient with new cauterizations, with an electric scalpel and/or thread ligatures, 4) as known, upon exiting the parotid gland, the branches of the facial nerve (7th cranial pair), the nerve responsible for the face mobility, become superficial, whereby the cauterizations performed on the subcutaneous tissue might damage these nerve ends, and where the same damage might arise from the use of the scalpel or the scissors (sectioning). It is not rare that, with the use of the cited procedures, the patient develops a pull of the lip to one side due to injury of branches of the facial nerve, such injury being reverted in a few weeks in the majority of cases, however causing a great amount of discomfort to the surgical team and especially to the patient, 5) complications of the hematomas: the hematomas (formed by use of techniques based on scalpel or scissors), depending on their volume (sometimes quite large and deforming the face of the patient), as well as depending on the time from formation thereof until being attended to, might cause a significant amount of damage to the skin of the face, such as extensive cutaneous necrosis and also injuries of branches of the facial nerve due to compression.

If the formed hematoma also reaches the neck and is not drained in a short period of time, the whole skin of the face and neck will be infiltrated (purple), with a risk of necrosis, and the least consequence of this fact will be that the patient will spend several weeks treating the ecchymoses (purple blotches) and the facial and cervical (neck) edema.

All plastic surgeons consider the hematoma and injuries to the facial nerve to be the most serious factors of complication associated with facelift surgery (plastic surgery of the face).

The formation of hematomas extends, and sometimes doubles the surgery time, increasing the time of permanence in the hospital, burdening the patient and stressing the team, in addition to entailing costs in regard of various dressings and repeated surgical procedures, when cutaneous necrosis occurs. In these cases the hospital costs may increase to great extent.

The injuries incurred by the facial nerve cause the patient to postpone his or her return to normal activity, with correspondingly significant financial losses, depending on the patient's profession.

The device and method disclosed by the present invention are capable of remedying these disadvantages, particularly in the case of bleeding associated with facelift surgery procedures. With the use of the present invention there is obtained an improvement in the quality of the cutaneous cuts, less post-op edema, reduced surgery time, minimization of ecchymoses, prophylaxis of injuries to the facial nerve, and most of all, the post-op formation of hematomas is minimized.

SUMMARY OF THE INVENTION

In a first aspect the present invention refers to a surgical device for cutaneous detachment of face, leg, thigh, breast, abdomen and forehead. The device is made of a rigid material and comprises a stem, a supporting region and non-cutting, preferentially convex tips.

The configuration of the device according to the present invention when it is used to detach the skin of the face provides the supporting region centrally on the stem, and the configuration of the device when it is used to detach the skin of leg, thigh, breast and forehead provides the supporting region located at one of the ends of the stem, to provide an easier handling of the device by the surgeon.

In a second aspect the present invention refers to the surgical method for cutaneous detachment of face, leg, thigh, breast, abdomen and forehead using the surgical device to detach the skin of the face, the leg, the thigh, the breast, the abdomen and the forehead, according to the present invention.

DETAILED DESCRIPTION OF THE INVENTION

The surgical device for cutaneous detachment of the face, the leg, the thigh, the breast, the abdomen and the forehead according to the present invention comprises a rigid stem 1, one or two non-cutting, preferably convex tips 2, and a supporting region 3 which accommodates the fingers of the surgeon.

In the preferred modality of the present invention the stem 1 and the supporting region 3 are cylindrical.

The presently disclosed surgical device is preferably made of a metallic material, such as, for example, of aluminum, either or not plated with chrome, and stainless steel. Optionally, such device may be made of a plastic material, such as, for example, of acrylic. Other appropriate materials may also be used according to the instant invention, providing acceptable final results.

Preferably the length of the stem 1 varies between 30 and 40 cm and the thickness thereof varies between 1.5 and 20 mm and the diameter of the convex tip 2 varies between 1.0 and 20 mm.

During surgery, the surgeon has access to a set of devices according to the present invention, each having a different thickness varying, preferentially, between 1.5 and 20 mm. The surgeon uses the devices according to the present invention sequentially and in increasing order of diameter until achieving the desired cutaneous detachment.

To facilitate the handling of the surgical device, the supporting region 3 may be provided with ribs to provide a better grip.

Figure 1:
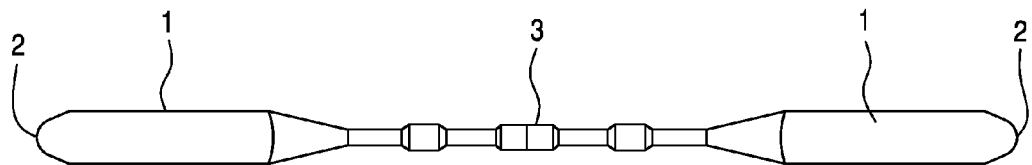
FIG. 1 shows the surgical device according to the present invention in its face detachment embodiment, with two convex non-cutting tips and having a thickness of 20 mm.
Figure 2:
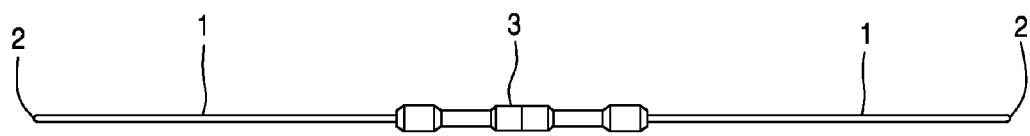
FIG. 2 shows the surgical device according to the present invention in its face detachment embodiment, with two convex non-cutting tips and having a thickness of 1.5 mm.

The supporting region 3 may be located at any point along the length of the stem 1. Preferentially, in order to facilitate the handling of the device by the surgeon, when the device is used for cutaneous detachment of the face, the supporting region is located at the center of the stem 1, dividing the same in two parts, as shown in FIGS. 1 and 2.

Figure 3:
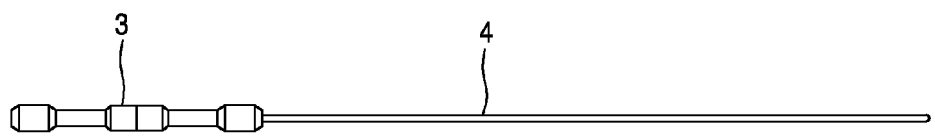
FIG. 3 shows the surgical device according to the present invention in its embodiment used to detach the skin of the leg, the thigh, the breast, the abdomen and the forehead, with only one convex non-cutting tip.

With the same purpose of facilitating the handling of the device by the surgeon, when the device is used for cutaneous detachment of the leg, the thigh, the breast, the abdomen and the forehead, in the preferred modality of the present invention, the supporting region is located at one of the ends of the stem 4, as shown in FIG. 3.

Surgical Method

The invention also refers to the surgical procedures performed for subcutaneous detachment of the face, the leg, the thigh, the breast, the abdomen and the forehead.

Face-Lifting

There is described a pioneering technique for prophylaxis of hematomas and injuries to the facial nerve in surgical facelift procedures, using for that purpose the device that is the object of the instant invention, as described hereinabove.

Figure 4:
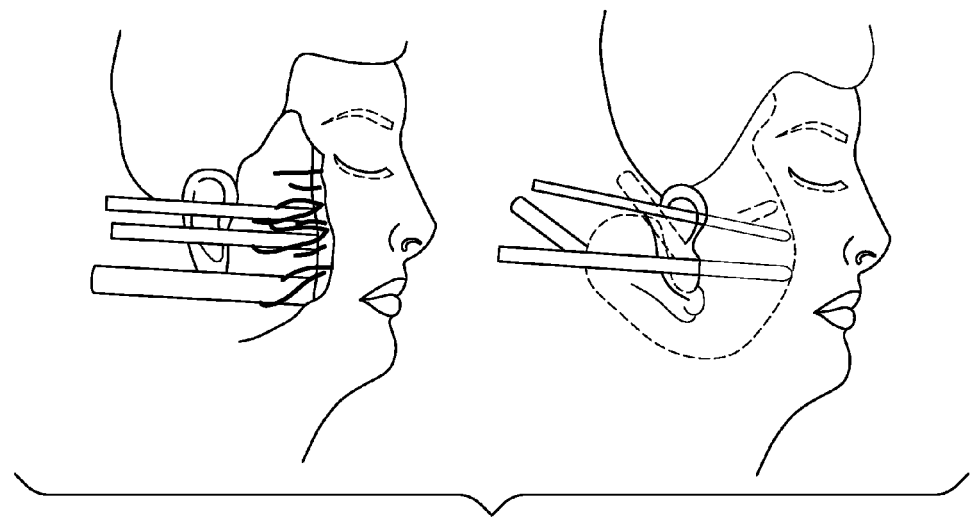
FIG. 4 shows the insertion of the detaching devices into the three incisions made for cutaneous detachment. Stretching, tapering and rupture of the vessels by the action of the detaching devices.

The cited device allows the sectioning of the vascular intima, which launches a migration of blood platelets to the injured area, followed by an immediate formation of blood clots, which are retained within the vascular extremities, which were subjected to progressive stretching with substantial tapering of their lumens prior to sectioning, thereby obtaining the incarceration of the clots in the extremities of the sectioned vessels, preventing the blood from flowing (FIG. 4).

Initially there is performed a previous marking of the patient in bed, in a sitting position, defining the areas for facelift with superficial musculoaponeurotic system (SMAS)-platysma treatment (SMAS means a set of tissues located beneath the skin that involves the face and neck).

Figure 5:
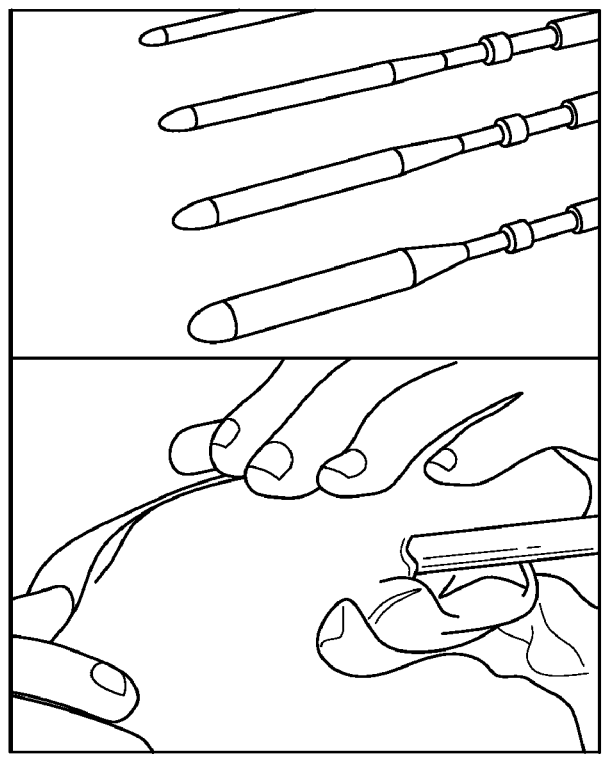
FIG. 5 shows the surgical devices of the present invention ("Dilson Luz detachment devices")—enlarged view of the active part of the facial detachers with their different diameters and application thereof in Facelift surgery.
Figure 6:
FIG. 6 is a photograph depicting the region named "ear shadow" located at the retro auricular area, upon detachment using scalpel and/or scissors.

In the Operating Room, with the patient lying on his or her back and under sedation, always with an anesthesiologist in attendance: 1) One half of the face is infiltrated with a lidocaine solution at 0.5% plus bupivacaine at 0.125% and with a solution of epinephrine at $1/200.000$ in a volume variable between 150 and 200 ml for the entire face; 2) After the blepharoplasties, when indicated, there are initiated the facelift incisions through the previously anaesthetized half-face; 3) Two incisions of approximately 2.5 cm (two and one half centimeters) are made in the preauricular area and one other incision of equal length is made in the retro auricular area, all performed along the line previously marked for the facelift procedure; 4) There is performed the technique per se, that is to say, there is initiated the cutaneous detachment using the thinnest rod with a thickness of 2 mm (two millimeters), passing the rod through the entire facial area that was previously marked, almost always including detachment of the cervical region; 5) Subsequently there are passed thicker rods through that same area, that is, rods with thicknesses of 4 mm (four millimeters), 6 mm (six millimeters), 8 mm (eight millimeters), consecutively until completing the cutaneous detachment of the half-face using rod thicknesses up to 20 mm when necessary; FIG. 5). With approximately 90% of the hemi-face already detached using the rods, there is noted a minimal amount of bleeding which in most cases obviates the need to cauterize; 7) The remaining 10% represent the region named the "ear shadow" (located in the retro auricular region, extending from the ear lobe until the beginning of the occipital hairy region, measuring in average 6 to 7 cm in length and having a thickness below the retro auricular canal of approximately 2.5 cm, FIG. 6, which is detached using the conventional method with scalpel and/or scissors, for the purpose of achieving a thicker cut for prophylaxis of cutaneous suffering in this area; 8) The temporal area is incised with a scalpel and there is performed the subaponeurotic detachment of the region using a medium-thickness rod with a thickness of 10 mm; 9) Following the complete detachment of the hemi-face, there is performed hemostasy by cauterization, which requirement is restricted to the area named the "ear shadow" and the region of the temporal vessels wherein were used the scissors or the scalpel; 10) The procedure follows with the resections and the SMAS-platysma treatment; 11) The redundant skin is sectioned using scissors for the hairless skin and scalpel for the hairy scalp areas; 12) Suturing is also performed using the conventional method, with details for the formation of the new tragus; 13) A tubular aspiration drain is applied to the detached area and should be removed within 12 and 48 hours thereafter; 14) An identical surgical procedure is performed on the other hemi-face; 15) Finally there is made an incision with a length of approximately 3 cm, parallel and located below the mentonian dimple, with previous liposuction when necessary, which detachment is performed with scissors for better identification and treatment of the platysmal bands, where after the cutaneous suture there is introduced the laminar drain. 16) There is applied the classic occlusive dressing with cotton and crepe band, which will be changed within the first 12 to 24 hours.

Surgery Cases and Results 20 (twenty) patients were subjected to this new technique, of which 02 (two) were male patients and 18 (eighteen) were female patients, with ages ranging from 43 to 72 years old, with post-surgery follow-ups of 02 days to 30 months, all patients having undergone facelift surgery and a few related procedures.

Figure 7A:
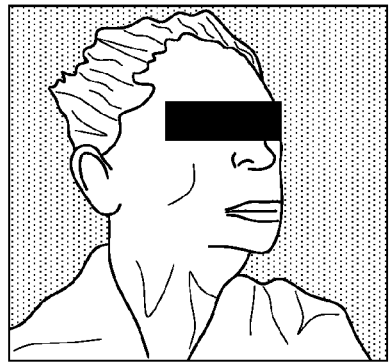
FIG. 7 shows photographs of the patient in the 2nd day after surgery subject to Facelift, treatment of platysmal bands and peeling at the orbicular region of the eyes.
Figure 7B:
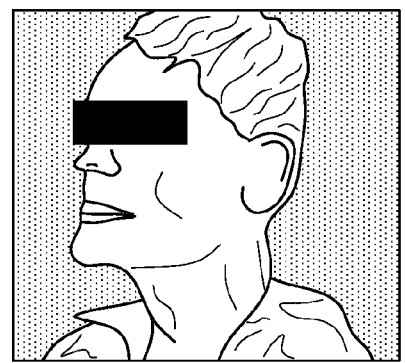
Figure 8A:
FIG. 8 shows photographs taken on the 4th day after surgery subject to Facelift, treatment of platysmal bands and peeling at the orbicular region of the eyes.
Figure 8B:
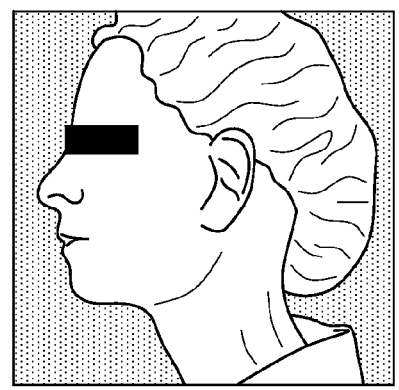

Evaluations conducted at immediate and late post-op times disclosed a minimum edema and excellent skin texture, such benefit deriving from the small amount of damage inflicted to the skin through detachment using rods. There is thus noted a significant reduction of ecchymoses. FIGS. 7 and 8. With associated facelift and peeling procedures there was noted a greater extent of edema, however without the presence of ecchymoses. FIGS. 7 and 8. In the presently reported series there was not any case of hematoma, significant ecchymoses or facial nerve injuries (temporary or persistent). There was reported one case of infection identified on the 3rd day post-op, incurred by a patient with diabetes, which was treated without incurring any sequel. The detachment using rods provided dermo-adipose flaps of good thickness, excellent blood perfusion and low amount of damage to the tissues. The cutaneous detachment of the hemi-face requires a brief time of 15 to 25 minutes in the areas where the rods are used, whereby it is ascertained that only few vessels require cauterization. One of the patients developed a post-op residual edema that persisted for three weeks, such fact believed to have been caused by the hypertension crisis that occurred while performing surgery and having persisted for the following 48 hours, which treatment left no sequel. In the region named the "ear shadow", after previous marking there is performed cutaneous detachment using a scalpel, in order to achieve a thicker cutting in this area, thereby preventing the appearance of retro auricular necrosis. There was finally noted that the facial detachment using metallic rods with increasing thicknesses prevents sectioning of facial nerve ends, and since cauterization is all but waived in the areas detached using this method, there will consequently not be caused to occur thermal damages in the nerve ends as frequently occur in traditional cutaneous detachment procedures.

Leg Skin Detachers

There is performed a 4 cm incision slightly below the posterior fold of the knee. 2. There is then identified the fascia which involves the leg muscles. 3. Lateral cutaneous marking of the locations for detachment and fasciotomy. 4. Subcutaneous and sub-facial detachment using the detachers, until approximately 8 cm above the ankle bones, both internal and external. 5. The cutting area of the fasciotome is fit in the beginning of the fascia, in both sides, internal and external of the leg 6. Upon completing the internal and external fasciotomy, caring to leave a substantially wide fascia band, there is placed the sub-facial prosthesis, without risk of compartimental syndrome, that is, the prosthesis will stay in place without causing symptoms of compression in the leg. 7. As a result, there is achieved a lesser degree of post-op edema, the patient suffers less pain, less discomfort in walking, and above all there is obviated the risk of compartimental syndrome. The leg skin detachers in fasciotome are recommended for emergency procedures in vascular and orthopedic surgery, for treatment of patients exhibiting compartmental syndrome.

Figure 9A:
FIGS. 9-A, 9-B and 9-C show photographs of one patient (age 56) prior to surgery.
Figure 9B:
Figure 9C:

There is concluded that the technique developed in accordance with the present invention is a pioneering technique for cutaneous detachment of the face using metallic rods of varying and increasing thicknesses applied in facelift surgery. With the use of this procedure there is obtained a reduction of vascular cauterization requirements, reduced surgery time, excellent perfusion of the facial skin flaps, significant decrease of ecchymoses, prophylaxis of facial nerve injuries and above all, prophylaxis of post-op hematoma formation. FIGS. 7 to 9. Equivalent results are achieved with the use of these devices in procedures for cutaneous detachment of the leg, the thigh, the breast, the abdomen and the forehead.

The examples provided herein are not intended to exhaust the practical applications of these devices, as obviously the same may be used in various other surgical situations not described hereinabove but nonetheless covered by the scope of the present invention.

The invention claimed is:

1. A method for cutaneous tissue detachment, comprising the steps of:
   a) marking an area of tissue for cutaneous tissue detachment;
   b) forming at least two cutaneous tissue incisions of approximately 2.5 cm each;
   c) passing a first rod having a first diameter through the entire marked cutaneous tissue area;
   d) passing at least a second rod having a second rod diameter greater than the first rod diameter through the entire marked cutaneous tissue area;
   e) tapering at least one blood vessel in the marked tissue area with at least one of the first and second rods;
   f) sectioning the at least one tapered blood vessel after progressively stretching the tapered blood vessel with at least one of the first and second rods;
   g) causing formation of one or more blood clots in a tapered portion of the sectioned vessel, and
   incarcerating the one or more formed blood clots in an extremity of the sectioned vessel with at least one of the first and second rods until blood no longer flows past the one or more incarcerated clots,
   wherein steps c) through g) are performed without cauterization.

2. The method of claim 1, wherein steps c) through g) are performed without using scissors or a scalpel.

3. The method of claim 1, wherein steps c) through g) are repeated until approximately 90% of the marked tissue area is detached from the underlying fatty tissue.

4. The method of claim 1, wherein the first and second rod diameters are between 1.5 mm and 20 mm.

5. The method of claim 1, wherein each rod comprises:
   a rigid stem (1), comprising one or two non-cutting tips (2); and
   a supporting region (3).

6. The method of claim 5, wherein each rod is made of a metallic material.

7. The method according to claim 6, wherein the metallic material comprises aluminum.

8. The method according to claim 7, wherein the metallic material comprises chrome-plated aluminum.

9. The method according to claim 6, wherein the metallic material comprises stainless steel.

10. The method of claim 5, wherein each rod is made of a plastic material.

11. The method according to claim 10, wherein the plastic material comprises acrylic.

12. The method according to claim 5, wherein the length of the stem (1) varies between 30 and 40 centimeters.

13. The method according to claim 5, wherein the thickness of the stem (1) varies between 1.5 and 20 millimeters.

14. The method according to claim 5, wherein the stem (1) is cylindrical.

15. The method according to claim 5, wherein the tip (2) is convex.

16. The method according to claim 15, wherein the diameter of the tip (2) varies between 1.0 and 20 millimeters.

17. The method according to claim 5, wherein the supporting region (3) is ribbed to provide a better grip in handling of the device.

18. The method according to claim 5, wherein the supporting region (3) is provided in cylindrical shape.

19. The method according to claim 5, wherein the supporting region (3) is located at the central region of the device, dividing the stem (1) in two parts.

20. The method according to claim 5, wherein the supporting region (3) is located at one end of each rod, such that the stem (4) has one single part.

* * * * *